Jan. 21, 1941. H. H. OWENS Plant Pat. 442

FLOWERING DOGWOOD TREE

Filed Aug. 10, 1940

Inventor
H. H. Owens

By Robb & Robb
Attorneys

Patented Jan. 21, 1941

Plant Pat. 442

UNITED STATES PATENT OFFICE

442

FLOWERING DOGWOOD TREE

Hiram H. Owens, Barbourville, Ky., assignor to Stark Bro's Nurseries & Orchards Co., Louisiana, Mo.

Application August 10, 1940, Serial No. 352,166

1 Claim. (Cl. 47—59)

This discovery relates to a new and distinct variety of flowering dogwood tree, originating as a chance seedling, and having as its primary feature of novelty, the giant size of flower.

Figure 1:
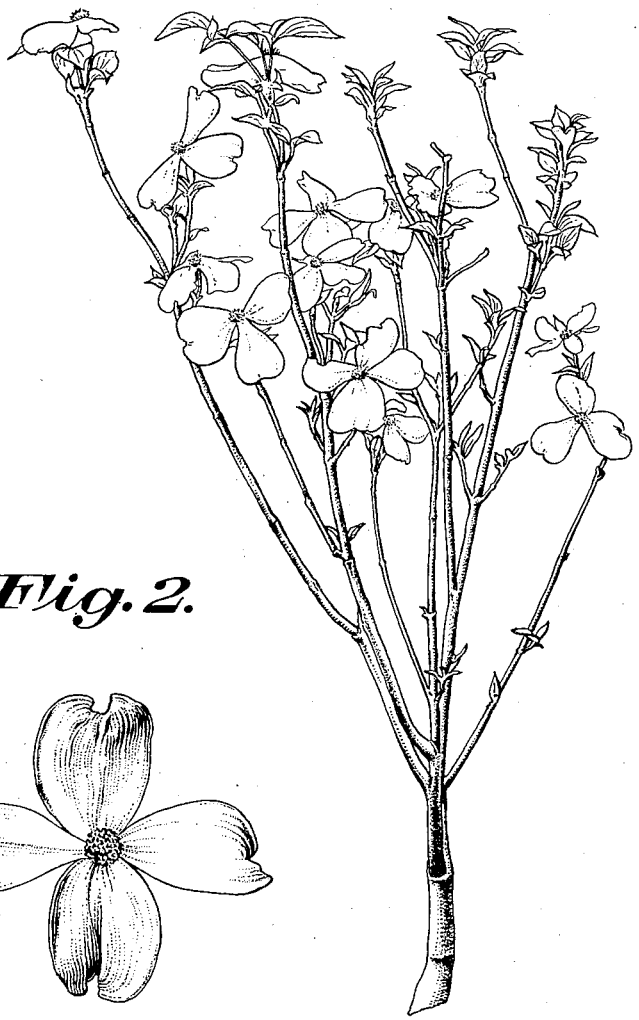
Figure 2:
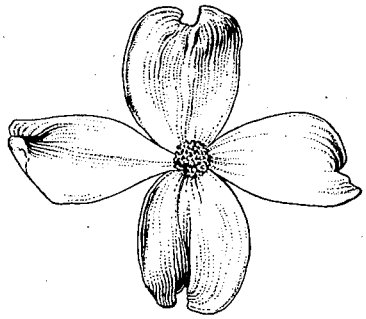

Figure 1 of the accompanying illustration shows a two-year second generation tree, and Figure 2 is an illustration of a single bloom more particularly defining its shape or form on a reduced size basis. The purpose of the illustration is to show the unusual attractiveness and proportions of the bloom of this new variety of dogwood. The observations on which this description is based were made in the test gardens of Stark Bros. Nurseries in Missouri.

This new variety by careful comparison, when grown under comparable conditions, resembles most nearly the well known Cornus Florida Dogwood, there appearing to be no difference in the wood, color of bark, leaf structure, etc., of the two plants. However, there are two important differences which indicate the distinctiveness of the present variety, namely, the large size of the flower or bract, which reproduces true to type in succeeding generations, and the late time of blooming which is about ten days later than Cornus Florida, also a fixed characterstic.

By way of comparison of the size of the bract, the Cornus Florida variety usually measures from three to four inches across, while the present variety measures from four to six inches across.

The bloom is white in color and is unusual not only in respect of its size but also of its shape in that the bracts appear to be more linear and not so rounded as the native species. It also seems that the disc flowers in the center are in a much smaller cluster than is usually the case in the native species, the cluster of disc flowers in this instance being less than one-fourth of an inch in diameter.

The bracts may be described as obovate with cordate apex and broader cuminate base.

I claim:

A new and distinct variety of flowering dogwood tree characterized as to novelty by the large size and shape of its bracts and the late season of blooming, substantially as shown and described.

HIRAM H. OWENS.